(12) United States Patent
Tazuke et al.

(10) Patent No.: US 8,035,810 B2
(45) Date of Patent: Oct. 11, 2011

(54) SURFACE PLASMON RESONANCE SENSOR CHIP

(75) Inventors: Atsushi Tazuke, Kyoto (JP); Daisuke Niwa, Kyoto (JP); Yoshikatsu Miura, Kyoto (JP); Dai Ohnishi, Kyoto (JP)

(73) Assignee: Rohm Co., Ltd., Kyoto (JP)

( * ) Notice: Subject to any disclaimer, the term of this patent is extended or adjusted under 35 U.S.C. 154(b) by 88 days.

(21) Appl. No.: 12/365,307

(22) Filed: Feb. 4, 2009

(65) Prior Publication Data
US 2009/0195783 A1    Aug. 6, 2009

(30) Foreign Application Priority Data
Feb. 5, 2008  (JP) .................... 2008-025141 (P)

(51) Int. Cl.
*G01N 21/01*   (2006.01)
(52) U.S. Cl. ..................................... 356/244
(58) Field of Classification Search .......... 356/244–246, 356/445–448
See application file for complete search history.

(56) References Cited

U.S. PATENT DOCUMENTS

| | | | |
|---|---|---|---|
| 7,671,996 B2* | 3/2010 | Niwa et al. ............... | 356/445 |
| 2006/0274314 A1* | 12/2006 | Thomsen et al. .......... | 356/445 |
| 2009/0066962 A1 | 3/2009 | Niwa et al. | |
| 2009/0209028 A1* | 8/2009 | Dong et al. ............... | 435/287.2 |

FOREIGN PATENT DOCUMENTS

| | | |
|---|---|---|
| JP | 2003-042944 | 2/2003 |
| JP | 2003-279476 | 10/2003 |
| JP | 2006-250668 | 9/2006 |

OTHER PUBLICATIONS

K. Kuhira et al., "Theoretical understanding of an absorption-based surface plasmon resonance sensor based on Kretchmann's theory.", Anal. Chem. 74(3):696-701 (2002).
Shumaker-Parry J.S. et al., "Microspotting streptavidin and double-stranded DNA arrays on gold for high-throughput studies of protein-DNA interactions by surface plasmon resonance microscopy", Anal. Chem., 76(4):918-929 (2004).

* cited by examiner

*Primary Examiner* — Michael P Stafira
(74) *Attorney, Agent, or Firm* — Fish & Richardson P.C.

(57) ABSTRACT

A surface plasmon resonance sensor chip includes: a first dielectric layer; a metal layer disposed on the first dielectric layer; and a second dielectric layer covering the metal layer, the chip being provided with an opening that makes a part of a surface on the side of the second dielectric layer of the metal layer be exposed, and allows a measurement sample and the surface on the side of the second dielectric layer to contact each other, wherein an organic molecule film is provided at least one of between the first dielectric layer and the metal layer, and between the metal layer and the second dielectric layer.

10 Claims, 5 Drawing Sheets

SURFACE PLASMON RESONANCE SENSOR CHIP

BACKGROUND OF THE INVENTION

1. Field of the Invention

The present invention relates to a surface plasmon resonance sensor chip utilizing a surface plasmon resonance phenomenon, and in particular, to a surface plasmon resonance sensor chip for use in a biological function analysis using in a vitro sample and in an environment measurement.

2. Description of the Background Art

Currently, in biochemical and medical fields, it is requested to find out a correlation between bioactive molecules in a biological body with high accuracy. Accordingly, there is a need for sensors capable of measuring progress of biochemical reaction of bioactive molecule or the like with high accuracy, and having a small size, and the research is advanced. Among such sensors, a method using a light for measurement is excellent in the aspect of sensitivity, and various techniques including a colorimetric method, a fluorescence method and a luminescence method have been developed. However, sensors using these techniques are bulky, and find a report that quenching phenomenon may occur due to color degradation of pigment. Also sensitivity in measurement by these techniques seems to be reaching a peak. Also many of sensors that are mainly used at present are so designed that the measurement is conducted in the condition that a measurement sample is dispersed in a solution, and according to such a design, a certain or longer optical path length is required. This makes it difficult to miniaturize the sensor.

In light of this, a sensor using such a sensing method that involves immobilizing a biological molecule on a substrate, and measuring reaction occurring on or near the substrate surface is recently proposed. In particular, sensors using a surface plasmon resonance spectroscopy attract attention because of excellent sensitivity and possibility of miniaturization (see, for example, K. Kurihara et al., Anal. Chem. 74(3): 696-701 (2002) (Non-Patent Document 1) and Shumaker-Parry J S et al., Anal. Chem. 76 (4):918-929 (2004) (Non-Patent Document 2)).

FIG. 3 is a schematic perspective view of one exemplary embodiment of a sensor utilizing a surface plasmon resonance phenomenon.

In the following, description will be made based on FIG. 3. A sensor shown in FIG. 3 includes a light source 80, a prism 81, a dielectric substrate 82, and a metal film 84, and dielectric substrate 82 is covered with metal film 84, and an antibody 85 serving as a receptor is immobilized on a surface of metal film 84. And it is possible to measure the quantity of a target molecule 86 that specifically binds to antibody 85 in a measurement sample.

First, an incident light λ1 is caused to enter dielectric substrate 82 covered with metal film 84, from light source 80 through prism 81. Incident light λ1 passes through dielectric substrate 82 and is then reflected at metal film 84, and an outgoing light λ2 arises through prism 81. At this time, when incident light λ1 and outgoing light λ2 are set at a certain incident angle and at a certain reflection angle, a surface plasmon resonance is observed in a boundary face between metal film 84 and dielectric substrate 82. And when target molecule 86 binds to immobilized antibody 85 in the condition that incident light λ1 and outgoing light λ2 are set so that the surface plasmon resonance is observed, the surface plasmon resonance will change (see, for example, Japanese Patent Laying-Open No. 2003-279476 (Patent Document 1) and Japanese Patent Laying-Open No. 2003-042944 (Patent Document 2)).

However, in conventional surface plasmon resonance sensors, it is necessary to arrange a chip and an optical system so that certain incident and reflection angles are provided for enabling entry of incident light λ1 through prism 81 or a transparent substrate of quartz or the like. This makes significant miniaturization difficult. It is known in principle that a loss arises in efficiency of occurrence of the surface plasmon resonance because incident light λ1 transmits to dielectric substrate 82 covered with metal film 84 through prism 81 or the like.

FIG. 4 is a schematic perspective view of one exemplary embodiment of a sensor utilizing a transmission-type surface plasmon resonance. FIG. 5 is a schematic section view showing a cross-section of the sensor in FIG. 4. FIG. 6 is a schematic section view showing a cross-section as another form of the sensor in FIG. 4.

In the following, description will be made based on FIGS. 4 to 6. In order to alleviate the problem as described above, the sensor as shown in FIG. 4 and FIG. 5 has been proposed at present. The sensor shown in FIG. 4 includes a chip 100 and a laser 60 serving as a light source. Chip 100 has a first dielectric layer 52, a metal layer 54 disposed on first dielectric layer 52, and a second dielectric layer 53 covering metal layer 54. Chip 100 is provided on a substrate 51. Chip 100 is provided with an opening for making a part of a surface on the side of second dielectric layer 53 of metal layer 54 be exposed and allowing a measurement sample and the surface to contact each other. Metal layer 54 at the opening is immobilized with an antibody 55 serving as a biological molecule which is to react with a target molecule contained in a measurement sample. Laser 60 emits a laser light 61 and laser light 61 enters from one end of metal layer 54 horizontally with respect to metal layer 54. Laser light 61 travels in the longitudinal direction of metal layer 54 serving as a waveguide, and outgoes from the other end through metal layer 54. Then an outgoing light 71 outgoing from the other end is detected.

According to this surface plasmon resonance sensor, it is possible to resolve arranging an angle between a chip and a light source, and to alleviate a light transmission loss at the prism.

Here, the surface plasmon resonance sensor as shown in FIG. 4 requires such a structure that a metal layer is sandwiched between dielectric members. In such a structure, relationship in a refractive index and adhesion between the dielectric member and the metal layer greatly influence on a performance of the surface plasmon resonance sensor. The surface plasmon resonance sensor as shown in FIG. 4 and FIG. 5 faces the problem that a transmission loss arises due to poor adhesion between the metal layer and the dielectric member, resulting in reduction in sensitivity in measurement. As a method of improving the adhesion, there is known a surface plasmon resonance sensor as shown in FIG. 6 in which different kind of metal 57 is sandwiched between the metal layer and the dielectric member as shown in FIG. 5, however, it is proved that a transmission loss arises due to a transmission-type surface plasmon resonance absorption by different kind of metal 57, and sensitivity of the surface plasmon resonance sensor is deteriorated accordingly.

At present, a surface plasmon resonance sensor for use as a biosensor is also proposed (Japanese Patent Laying-Open No. 2006-250668 (see Patent Document 3)).

SUMMARY OF THE INVENTION

From the aforementioned problems, there is a need for a substance having the following characteristics for improving sensitivity of a sensor: 1) improving adhesion between a metal and a dielectric member, 2) not a absorbing transmission-type surface plasmon polariton, 3) having a refractive index that is generally equal to that of dielectric member, and 4) being too thin to attenuate plasmon.

Therefore, it is an object of the present invention to provide a surface plasmon resonance sensor chip that improves adhesion between a metal layer and a dielectric layer and does not absorb a surface plasmon resonance in order to alleviate a transmission loss of the surface plasmon resonance on the metal layer.

MEANS FOR SOLVING THE PROBLEM

The present invention relates to a surface plasmon resonance sensor chip, including: a first dielectric layer; a metal layer disposed on the first dielectric layer; and a second dielectric layer covering the metal layer, the chip being provided with an opening that makes a part of a surface on the side of the second dielectric layer of the metal layer be exposed, and allows a measurement sample and the surface on the side of the second dielectric layer to contact each other, wherein an organic molecule film is provided at least one of between the first dielectric layer and the metal layer, and between the metal layer and the second dielectric layer.

Preferably, in the surface plasmon resonance sensor chip of the present invention, an organic molecule forming the organic molecule film is an organic silane compound having at least one of a mercapto group and an amino group.

Preferably, in the surface plasmon resonance sensor chip of the present invention, the metal layer is formed of at least one of gold, silver, aluminum, copper, titanium, nickel, chromium and platinum.

Preferably, in the surface plasmon resonance sensor chip of the present invention, the first dielectric layer and the second dielectric layer are formed of at least one of $SiO_2$, SiON, GaAs, InP, Si, glass, quartz, alumina, silicone, polyurethane, polystyrene, polytetrafluoroethylene, polyethylene and $Si_3N_4$.

It is possible to provide a surface plasmon resonance sensor chip that improves adhesion between a metal layer and a dielectric layer and does not absorb a surface plasmon resonance in order to alleviate a transmission loss of a surface plasmon resonance on the metal layer.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
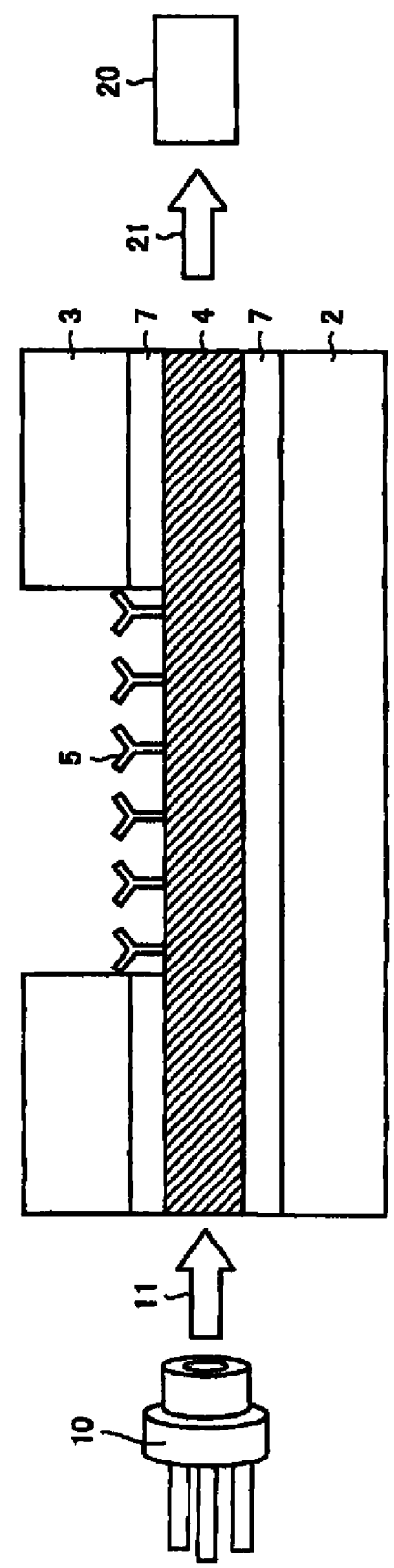
FIG. 1 is a schematic section view showing one exemplary embodiment of the present invention.

In the following, preferred embodiments of the present invention will be described based on attached drawings. In these drawings, an identical or a corresponding part is denoted by the same reference numeral, and repeated description thereof is not given. Length, size, width and the like dimensional relations in drawings are appropriately changed for clarity and simplification of drawings, and do not represent actual dimensions.

FIG. 1 is a schematic section view showing one exemplary embodiment of the present invention. In the following, based on FIG. 1, a basic structure of a surface plasmon resonance sensor chip according to the present invention will be described, and then an organic molecule film will be described, and then materials and the like of members other than the organic molecule film in the surface plasmon resonance sensor chip will be described.

<<Basic Structure>>

As shown in FIG. 1, a surface plasmon resonance sensor chip of the present invention includes at least a first dielectric layer 2, a metal layer 4 disposed on first dielectric layer 2, and a second dielectric layer 3 covering metal layer 4. And, the surface plasmon resonance sensor chip is provided with an opening for making a part of a surface on the side of second dielectric layer 3 of metal layer 4 be exposed and allowing a measurement sample and the surface to contact each other. In the present exemplary embodiment, metal layer 4 at the opening is immobilized with an antibody 5 serving as a biological molecule that reacts with a target molecule contained in a measurement sample. A substance such as antibody 5 that reacts with a target molecule in a measurement sample may be appropriately chosen.

And in the present exemplary embodiment, an organic molecule film 7 is provided between first dielectric layer 2 and metal layer 4, and between metal layer 4 and second dielectric layer 4. When a laser light 11 emitted from a laser 10 enters horizontally with respect to metal layer 4 from one end of metal layer 4, laser light 11 travels in the longitudinal direction of metal layer 4 functioning as a waveguide, and outgoes from the other end through metal layer 4.

A refractive index near a top face of metal layer 4 changes before and after bringing a measurement sample into contact with the opening. In the present invention, by analyzing the change in the refractive index by a detector 20 that detects an outgoing light 21, a target molecule in the measurement sample is measured. Preferably, metal layer 4 is entirely covered with second dielectric layer 3 in the part other than the opening, however, there may be a part that is not covered.

A thickness of metal layer 4 is preferably in the range of 1 nm to 100 nm, and particularly preferably in the range of 10 nm to 40 nm. This is because when the thickness of metal layer 4 is less than 1 nm, formation of metal layer 4 may be difficult, and when the thickness of metal layer 4 is more than 100 nm, a surface plasmon resonance may not occur in metal layer 4. A short-side length of metal layer 4 is preferably in the range of 50 nm to 100 μm. This is because when the length is less than 50 mm, a surface plasmon resonance may not occur in metal layer 4, and when the length is more than 100 μm, a higher order surface plasmon that is less useful may abundantly occur. A longitudinal length of metal layer 4 is preferably in the range of 30 μm to 5 mm. This is because when the length is less than 30 μm, sufficient resolution (analytical ability) may not be obtained, and when the length is more than 5 mm, an intensity of outgoing light 21 may be too low.

Preferably, the opening is provided within the range of 10 µm to 5 mm in the longitudinal direction. This is because when it is less than 10 µm, a contact amount of measurement sample may be insufficient, while when it is more than 5 mm, the intensity of outgoing light 21 may be too low.

A thicknesses of first dielectric layer 2 and second dielectric layer 3 are not particularly limited, and for example, may be in the range of 100 nm to 100 µm.

<<Organic Molecule Film>>

In the present exemplary embodiment, organic molecule film 7 that promotes a binding between a metal layer and a dielectric layer and improves adhesion between first and second dielectric layers and metal layer is provided on the surface contacting with first dielectric layer 2 or on both surfaces contacting with the dielectric layers (including first and second) in metal layer 4.

An organic molecule forming organic molecule film 7 is preferably an organic silane compound having at least one of a mercapto group and an amino group, and is particularly preferably an organic silane compound having a mercapto group. This is because an organic molecule forming organic molecule film 7 is requested to be able to securely bind to metal layer 4 by binding of S of mercapto group or N of amino group, or by an organic silane molecule intermolecular hydrophobic interaction. When it is an organic silane compound having a mercapto group, a disulfide bond also contributes to the binding. Concrete examples of the organic molecule include 3-mercapto propyltrimethoxy silane, 3-mercapto propylmethyldimethoxy silane, 3-amino propyltriethoxy silane and (6-aminoxyl)aminopropyl trimethoxy silane.

Preferably, a refractive index of organic molecule film 7 is as close as those of first dielectric layer 2 and second dielectric layer 3. Preferably, the refractive indexes of organic molecule film 7, first dielectric layer 2 and second dielectric layer 3 are set within the range of 1.0 to 4.0.

Also a thickness of organic molecule film 7 is preferably, but not particularly limited to, 5 to 30 angstroms, for preventing the absorption of a surface plasmon resonance. Non-limiting exemplary form of organic molecule film 7 may be an organic monomolecular film. In the case of an organic monomolecular film, the organic molecule forming organic molecule film 7 may be one kind, or a mixture of two or more kinds. The organic monomolecular film is as thin as one molecule layer, and the refractive index thereof may be set similarly as is the case of dielectric layer depending on its structure.

Further, by forming organic molecule film 7, for example, it is possible to make a history of the surface without roughing the surface of first dielectric layer 2. The proportion at which organic molecule film 7 is covered may also be measured by an X-ray photoelectron spectroscopy. An appearance of a surface of organic molecule film 7 may be observed under an electron microscope or the like. Since the surface plasmon resonance sensor chip of the present exemplary embodiment is able to improve adhesion between first dielectric layer 2 and second dielectric layer 3, and metal layer 4 by having organic molecule film 7, measurement sensitivity of the surface plasmon resonance sensor chip is improved, and efficiency as a device is improved.

An organic molecule forming organic molecule film 7 preferably has a C3-C21 linear structure. Organic molecules of smaller than C3 are difficult to obtain and may fail to realize the effect of improving a binding between metal layer 4, and first dielectric layer 2 and second dielectric layer 3. With organic molecules of larger than C21, it is difficult to form a monomolecular film because of an interaction between organic molecules forming organic molecule film 7, and a contribution to improvement in adhesion between metal layer 4, and first dielectric layer 2 and second dielectric layer 3 may not be offered.

A length of the organic molecule forming organic molecule film 7 is preferably in the range of 0.5 nm to 3 nm. The length derives from a molecular weight of the organic molecule forming organic molecule film 7.

Adhesion between metal layer 4 and first dielectric layer 2 may be evaluated, for example, in accordance with "Methods of adhesion test for metallic coatings (JIS-H8504)". While organic molecule film 7 is provided in two positions in the present exemplary embodiment, provision of either one will suffice to obtain the effect of the present invention. It suffices that organic molecule film 7 is at least partly in contact with metal layer 4.

According to the present invention, by using the surface plasmon resonance sensor chip having excellent adhesion between metal layer 4, and first dielectric layer 2 and second dielectric layer 3 owing to organic molecule film 7, it is possible to provide bio sensing with higher sensitivity than ever before, and to detect or diagnose antigen-antibody reaction, gene mutation, gene-protein interaction, cell or protein function, identification of metabolic substance and the like with high accuracy.

If adhesion between metal layer 4, and first dielectric layer 2 and second dielectric layer 3 is poor, the surface plasmon resonance sensor chip may be easily broken due to physical factors such as impact, or chemical factors such as acid or alkali, however, according to the present invention, the surface plasmon resonance sensor chip can bear repeated uses and use in a severe conduction such as in an alkaline solution, and can be used for an environment measurement such as water examination.

<<Individual Members>>

Metal layer 4 is preferably formed of at least one of gold, silver, aluminum, copper, titanium, nickel, chromium and platinum, and is particularly preferably formed of either one of gold, silver and copper. These materials are likely to generate surface plasmon wave. Sulfur (S) and an amino group in the aforementioned mercapto group strongly bind to these materials, and contribute to improve adhesion power between metal layer 4, and first dielectric layer 2 and second dielectric layer 3.

First dielectric layer 2 and second dielectric layer 3 are preferably formed of at least one of $SiO_2$, SiON film (nitride oxide silicone film), GaAs, InP, Si, glass, quartz, alumina, silicone, polyurethane, polystyrene, polytetrafluoroethylene, polyethylene and $Si_3N_4$. This is because these materials have high transparency and are unlikely to absorb laser light 11 from laser 10. This is also because a refractive index can be set at an appropriate value for these materials. For example, $SiO_2$ may be formed on a surface of a silicon substrate (not shown) serving as a substrate, to render it first dielectric layer 2. A material of a substrate may be appropriately selected, and an oxide film may be formed on the substrate to give first dielectric layer 2 or second dielectric layer 3. Preferably, first dielectric layer 2 and second dielectric layer 3 are formed of materials that allow easy adjustment of molecular composition and adjustment of refractive index during formation, such as SiON or alumina.

As a biological molecule immobilized on metal layer 4 at the opening provided in second dielectric layer 3, protein such as enzyme and DNA may be exemplified besides antibody 5. Concrete examples of a target molecule that reacts with the biological molecule include an antigen that binds with the relevant antibody, a coenzyme that binds with the relevant enzyme, and protein or DNA that binds with the DNA. In other words, as the surface plasmon resonance sensor of the present invention, it is possible to use the techniques including sandwich immunoassay, avidin-biotin reaction system, hybridization and the like utilizing protein interaction, antibody-antigen reaction and gene reaction that are commonly used in a usual biosensor. The surface plasmon resonance sensor is able to measure how many target molecules are contained in the measurement sample. Preferably, outgoing light 21 is detected in detector 20 in the condition that an aggregate made up of the biological molecule and the target molecule is immobilized on a surface of metal layer 4. The measurement sample may be in a liquid state or in a gas state.

Even when the biological molecule is not provided, the surface plasmon resonance sensor chip in the present invention may be used for a measurement of a measurement sample.

A receptor intended for a specific olfactory sensation may be immobilized as the aforementioned biological molecule on metal layer 4. The surface plasmon resonance sensor having a sensor main body 50 to which a receptor intended for olfactory sensation is immobilized may be used as a mimetic biological body having a substantially equal efficiency with in vivo reaction. The receptor may be obtained by using a gene analysis and an engineering technique or by an extraction from living body. In the present invention, it is preferred to use the receptor having high purity as a result of purification. In immobilizing the receptor on metal layer 4, an antibody and the like may be used simultaneously.

It is also preferred to conduct a molecular modification treatment on the surface of metal layer 4 for immobilizing the biological molecule to metal layer 4. For example, in the molecular modification, it is preferred to conduct such a treatment as immobilizing alkyl silane, alkane thiol or the like molecule, or ionic polymer or the like molecule on the surface. Preferably, the molecule has at least one of —COOH, —$NH_2$, —$CF_3$, —$CH_3$, —CN, —$SO_3H$ and so on as a terminal functional group. As for the molecular modification treatment, various known techniques may be appropriately selected and used.

Preferably, substrate 1 is formed of one selected from $SiO_2$, GaAs, InP, Si, glass, quartz, silicone and plastic. As the glass, for example, porous glass and the like can be recited, and as the plastic, polyurethane and porous styrene can be exemplified.

As a laser serving as a light source, a semiconductor laser and an organic laser can be exemplified. As the organic laser, for example, the one described in H. Hajime Nakanonani et al., "Extremely low-threshold amplified spontaneous emission of 9,9'-spirobifluorene derivatives and electroluminescence from field-effect transistor structure" Adv. Funct. Mater., (in press 2007) may be used. In the present exemplary embodiment, when an organic laser is provided, the surface plasmon resonance sensor causes little environmental pollution when it is disposed of, and hence can be used as a disposable chip. The light source may be, for example, a light-emitting diode other than the laser. Preferably, wavelength of the laser light emitted by the laser falls within the range of 400 nm to 1600 nm. Also, in the present exemplary embodiment, 10% to 40% of laser light 11 emitted by the laser will be released outside the sensor main body rather than entering metal layer 4. Therefore, it is preferred to design an intensity of laser light 11 while taking the loss released outside into account.

<<Operation>>

In the following, description will be made based on FIG. 1. In the surface plasmon resonance sensor chip of the present invention, when laser light 11 is caused to enter from one end of metal layer 4 as described above, a surface plasmon resonance which is one kind of a surface plasmon resonance occurs on both surfaces of metal layer 4. In other words, a refractive index change on surface of metal layer 4 can be measured over time by the method that laser light 11 is caused to directly enter metal layer 4 serving as a waveguide. A measurement of the refractive index change is conducted at the opening. As the reaction between the biological molecule immobilized at the opening on surface of metal layer 4, and a target molecule proceeds, difference between a refractive index of first dielectric layer 2 and a refractive index of the surface of metal layer 4 increases, and a transmission loss also increases accordingly. By measuring an intensity of a light having attenuated by the transmission loss, and comparing it with a light quantity in an initial state, the refractive index of surface of metal layer 4 (near the top face) is determined, and from this an amount of target molecule having reacted with the biological molecule, for example, a quantity of antigen-antibody reaction is determined. When a target molecule in a measurement sample is modified with a nano particle, a similar phenomenon occurs at an amplified range, so that the amount of target molecule having reacted with the biological molecule can be sensed with higher sensitivity.

In the present exemplary embodiment, as the amount of antigen 6 that binds with antibody 5 increases, a refractive index of laser light 11 passing through metal layer 3 in the opening changes over time, and an intensity of a surface plasmon resonance occurring in metal layer 3 also changes. Outgoing light 21 outgoing from an end part of metal layer 3 serving as a waveguide is analyzed over time, and an amount of antigen 6 in the measurement sample can be calculated.

In the following, a surface plasmon resonance sensor according to another exemplary embodiment having the constituents as described above will be described. In the following exemplary embodiment, materials and the like described above can be appropriately selected.

<<Production Method>>

On a substrate (not shown), first dielectric layer 2 is formed by sputtering or the like. Next, the substrate is dipped in an ethanol solution containing a material of organic molecule film 7 for a certain time, and organic molecule film 7 is formed by sintering after cleaning. Alternatively, a resist may be applied on a surface of the substrate on which organic molecule film 7 is formed, and exposed to a light through a stripe mask followed by development, to obtain the SiON film and organic molecule film 7 having desired patterns.

Then, after forming metal layer 4 on the substrate by vapor deposition, cleaning is conducted to obtain a desired pattern of metal layer 4. Then organic molecule film 7 is appropriately formed on metal layer 4 in a similar manner as described above. Then and lastly second dielectric layer 3 is formed by sputtering or the like method. Through the above operation, a surface plasmon resonance sensor chip can be produced.

As is the case with the present exemplary embodiment, when a molecular modification treatment is made or antibody 5 is immobilized on the surface of metal layer 4, such a treatment may be conducted on the surface plasmon resonance sensor chip after formation of second dielectric layer 3.

In the following, the present invention will be described more specifically by way of examples, however the present invention will not be limited to these examples.

EXAMPLES

Example 1

In the following, description will be made based on FIG. 1.

<<Formation of First Dielectric Layer>>

First, on a substrate (not shown) made of silicon (Si), a SiON film (nitride oxide silicon film) having a thickness of 10 µm was formed as first dielectric layer 2.

<<Formation of Organic Molecule Film>>

Next, the substrate was dipped in a 20 mmol/L solution of 3-mercapto propyltrimethoxy silane (MPTMS) in ethanol for 2 hours. After dipping, the surface of the substrate was washed with ethanol and pure water, and baked at 110° C. for 120 seconds, to form organic molecule film 7. A resist was applied on the surface of the substrate on which organic molecule film 7 was formed, and exposed to a light through a stripe-like mask, followed by development to make the SiON film and organic molecule film 7 have desired patterns.

<<Formation of Metal Layer>>

Thereafter, metal layer 4 made of gold was formed by vapor deposition on the substrate. Film forming rate in the vapor deposition was 2 angstroms/second. A thickness of obtained metal layer 4 was 150 angstroms. Then the substrate on which metal layer 4 was formed was subjected to ultrasonic cleaning with acetone for 15 minutes, and lifted off for making metal layer 4 have a fine-line-like pattern.

<<Formation of Second Dielectric Layer>>

After lifting off, a SiON film having a thickness of 10 µm was formed as second dielectric layer 3 on the substrate by sputtering. Through the above operation, a surface plasmon resonance sensor chip was produced.

Comparative Example 1

A surface plasmon resonance sensor chip was produced in a similar manner as Example 1 except that a film made of titanium was formed on the substrate by sputtering vapor deposition rather than forming organic molecule film 7 in the process of <<Formation of Organic Molecule Film>> as described above.

[Evaluation of Adhesion]

Adhesion between first dielectric layer 2 and metal layer 4 in surface plasmon resonance sensor chips of Example 1 and Comparative Example 1 was evaluated.

For evaluation, a substrate directly after formation of metal layer 4 was used. Evaluation was conducted using a Scotch tape (registered) in accordance with "Methods of adhesion test for metallic coatings (JIS-H8504)".

While metal layer 4 failed to adhere with the scotch tape in the surface plasmon resonance sensor chip of Example 1, the metal layer in the surface plasmon resonance sensor chip of Comparative Example 1 adhered with the scotch tape. This proved that metal layer 4 and first dielectric layer 2 closely adhere to each other in the surface plasmon resonance sensor chip of Example 1.

[Evaluation of Measurement]

In the surface plasmon resonance sensor chip in Example 1, a transmission loss greatly changes due to a change in a refractive index in an upper region of substrate. Hence, it is possible to monitor composition of the solution being delivered by observation of change in the transmission loss. Therefore, the surface plasmon resonance sensor chip in Example 1 was used to measure whether composition in ethanol aqueous solution having various concentration can be discriminated or not.

With respect to the surface plasmon resonance sensor chip in Example 1, a flow channel pattern for liquid delivery (made of silicone) was arranged. Then, the opening and a measurement sample flowing in the flow channel pattern were made to be able to contact with each other. Then, as a measurement sample, pure water, 20% ethanol aqueous solution and 60% ethanol aqueous solution were delivered. At this time, a semiconductor laser emitting a light having a wavelength of 1550 nm was used for irradiating the surface plasmon resonance sensor chip with laser light 11. An injection light that had transmitted in the surface plasmon resonance sensor chip and released was measured.

Figure 2:
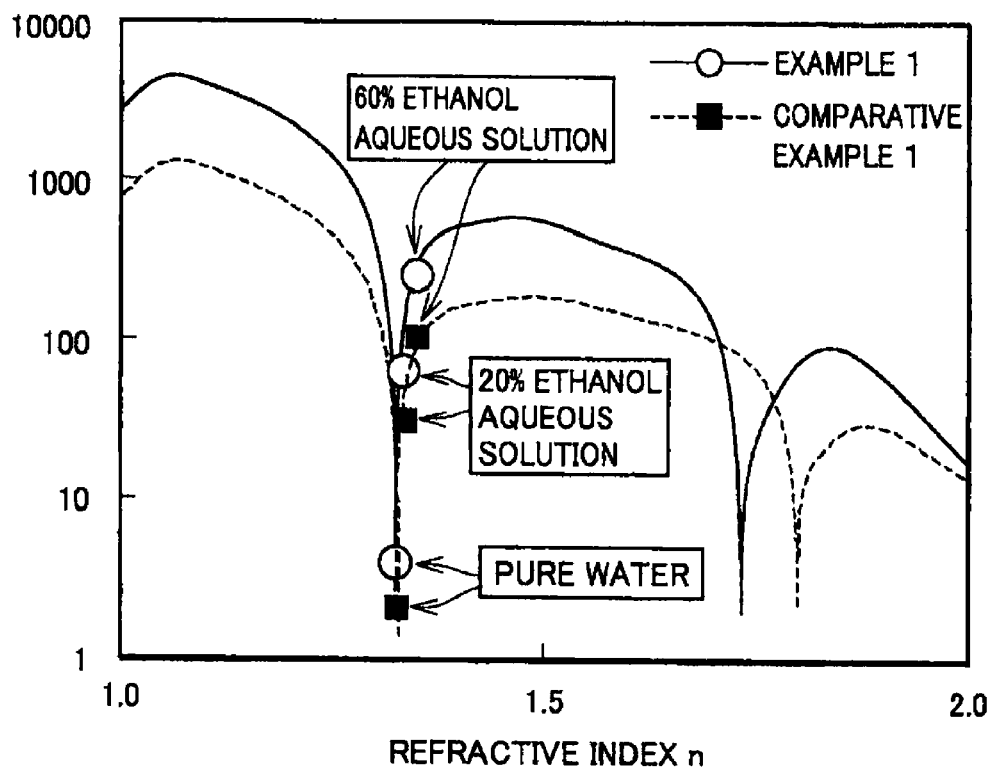
FIG. 2 is a view showing measurement results by a surface plasmon resonance sensors in Example 1 and Comparative Example 1.
Figure 3:
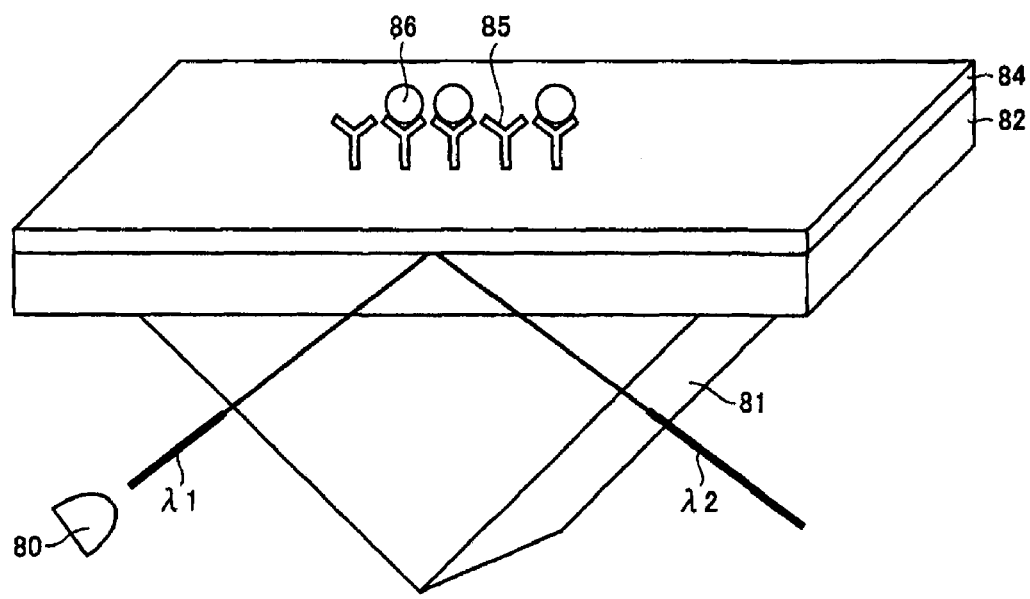
FIG. 3 is a schematic perspective view of one exemplary embodiment of a sensor using a surface plasmon resonance phenomenon.
Figure 4:
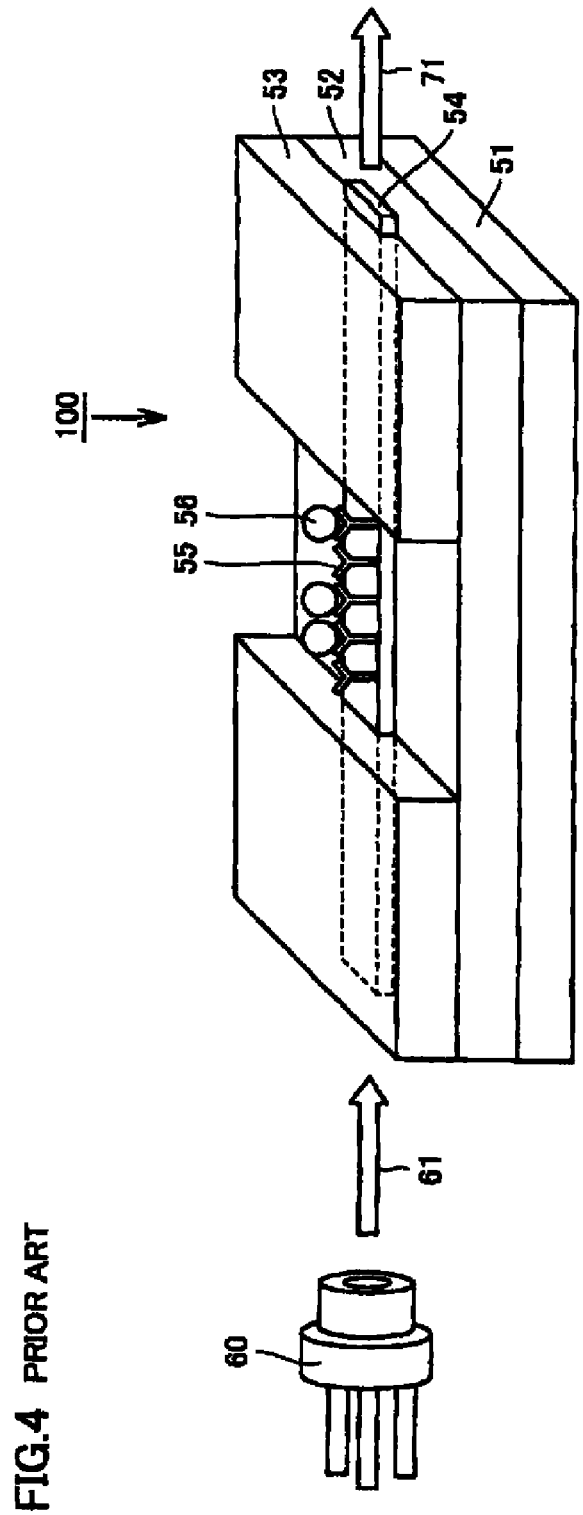
FIG. 4 is a schematic perspective view of one exemplary embodiment of a sensor utilizing a transmission-type surface plasmon resonance.
Figure 5:
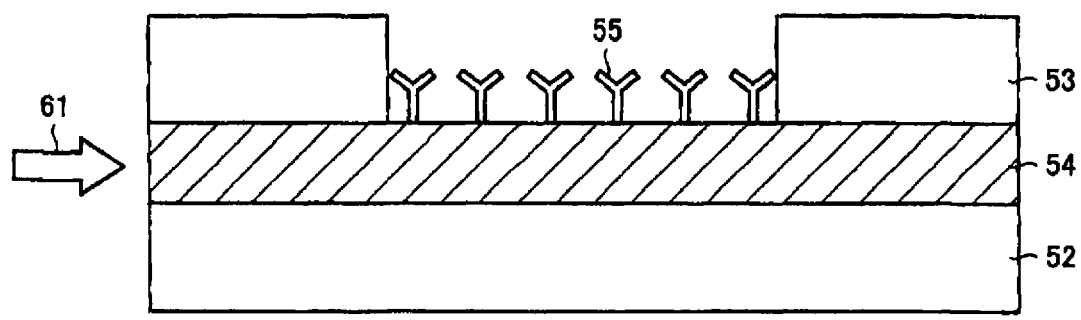
FIG. 5 is a schematic section view showing a cross-section of the sensor in FIG. 4.
Figure 6:
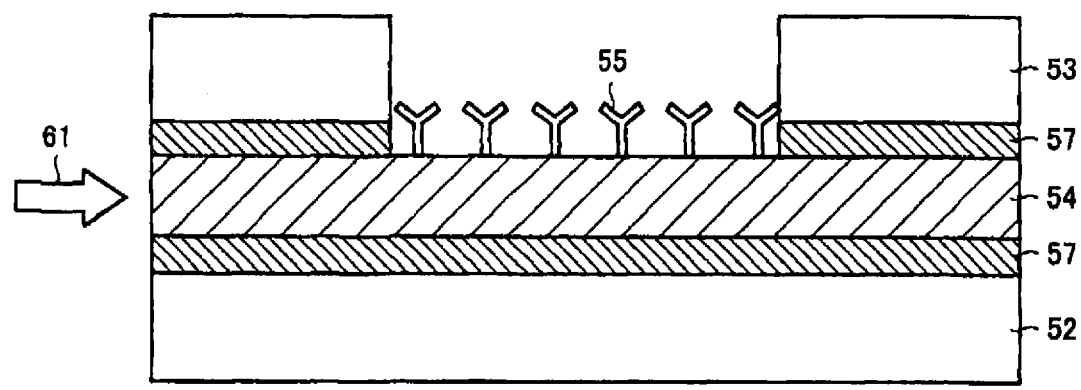
FIG. 6 is a schematic section view showing a cross-section as an another form of the sensor in FIG. 4.

FIG. 2 is a view showing measurement results by the surface plasmon resonance sensors in Example 1 and Comparative Example 1. In FIG. 2, the horizontal axis represents a change in a refractive index near the top face of metal layer 4, and the vertical axis represents a value of a transmission loss calculated from intensities of an incident light and an outgoing light and a moving distance of the incident light.

First, in Example 1, pure water was delivered into the flow channel, and a transmission loss measured at that time was 2.1 dB/mm. Next, 20% ethanol aqueous solution was delivered into the flow channel, and a transmission loss measured at that time was 82 dB/mm. Lastly, 60% ethanol aqueous solution was delivered into the flow channel, and a transmission loss measured at that time was 230 dB/mm.

In Comparative Example 1, pure water was delivered into the flow channel, and a transmission loss measured at that time was 1.9 dB/mm. Next, 20% ethanol aqueous solution was delivered into the flow channel, and a transmission loss measured at that time was 67 dB/mm. Lastly, 60% ethanol aqueous solution was delivered into the flow channel, and a transmission loss measured at that time was 104 dB/mm.

As interpretation of these results, it was found that a difference in a refractive index of ethanol aqueous solutions having different concentrations can be measured because a transmission loss of laser light 11 in the surface plasmon resonance sensor greatly changes due to a change in a refractive index near the surface of metal layer 4 in Example 1, as shown in FIG. 2.

The surface plasmon resonance sensor in Example 1 has higher sensitivity than the surface plasmon resonance sensor in Comparative Example 1, and concretely it offers sensitivity that is higher in the order of one digit.

Although the present invention has been described and illustrated in detail, it is clearly understood that the same is by way of illustration and example only and is not to be taken by way of limitation, the scope of the present invention being interpreted by the terms of the appended claims.

What is claimed is:

1. A surface plasmon resonance sensor chip, comprising:
   a first dielectric layer;
   a metal layer disposed on said first dielectric layer; and
   a second dielectric layer covering said metal layer,
   the chip being provided with an opening that makes a part of a surface on the side of said second dielectric layer of said metal layer be exposed, and allows a measurement sample and the surface on the side of said second dielectric layer to contact each other,
   wherein an organic molecule film is provided between at least one of said first dielectric layer and said metal layer, or between said metal layer and said second dielectric layer, and
   wherein an organic molecule forming said organic molecule film is an organic silane compound having at least one of a mercapto group and an amino group.

2. The surface plasmon resonance sensor chip according to claim 1, wherein said metal layer is formed of at least one of gold, silver, aluminum, copper, titanium, nickel, chromium and platinum.

3. The surface plasmon resonance sensor chip according to claim 1, wherein said first dielectric layer and said second dielectric layer are formed of at least one of SiO2, SiON, GaAs, InP, Si, glass, quartz, alumina, silicone, polyurethane, polystyrene, polytetrafluoroethylene, polyethylene and Si3N4.

4. The surface plasmon resonance sensor chip according to claim 2, wherein said first dielectric layer and said second dielectric layer are formed of at least one of SiO2, SiON, GaAs, InP, Si, glass, quartz, alumina, silicone, polyurethane, polystyrene, polytetrafluoroethylene, polyethylene and Si3N4.

5. The surface plasmon resonance sensor chip according to claim 1 comprising a first organic molecule film between said first dielectric layer and said metal layer, and a second organic molecule film between said metal layer and said second dielectric layer,
wherein each of the first and second organic molecule films comprises an organic silane compound having at least one of a mercapto group and an amino group.

6. A surface plasmon resonance sensor chip, comprising:
a first dielectric layer;
a metal layer disposed on said first dielectric layer; and
a second dielectric layer covering said metal layer,
the chip being provided with an opening that makes a part of a surface on the side of said second dielectric layer of said metal layer be exposed, and allows a measurement sample and the surface on the side of said second dielectric layer to contact each other,
wherein an organic molecule film is provided between at least one of said first dielectric layer and said metal layer, or between said metal layer and said second dielectric layer, and
wherein an organic molecule forming said organic molecule film is an organic silane compound having a mercapto group.

7. The surface plasmon resonance sensor chip according to claim 6, wherein said metal layer is formed of at least one of gold, silver, aluminum, copper, titanium, nickel, chromium and platinum.

8. The surface plasmon resonance sensor chip according to claim 6, wherein said first dielectric layer and said second dielectric layer are formed of at least one of SiO2, SiON, GaAs, InP, Si, glass, quartz, alumina, silicone, polyurethane, polystyrene, polytetrafluoroethylene, polyethylene and Si3N4.

9. The surface plasmon resonance sensor chip according to claim 7, wherein said first dielectric layer and said second dielectric layer are formed of at least one of SiO2, SiON, GaAs, InP, Si, glass, quartz, alumina, silicone, polyurethane, polystyrene, polytetrafluoroethylene, polyethylene and Si3N4.

10. The surface plasmon resonance sensor chip according to claim 6 comprising a first organic molecule film between said first dielectric layer and said metal layer, and a second organic molecule film between said metal layer and said second dielectric layer,
wherein each of the first and second organic molecule films comprises an organic silane compound having a mercapto group.

* * * * *